Sept. 29, 1936. R. T MULLER Plant Pat. 199
ROSE
Filed April 10, 1936
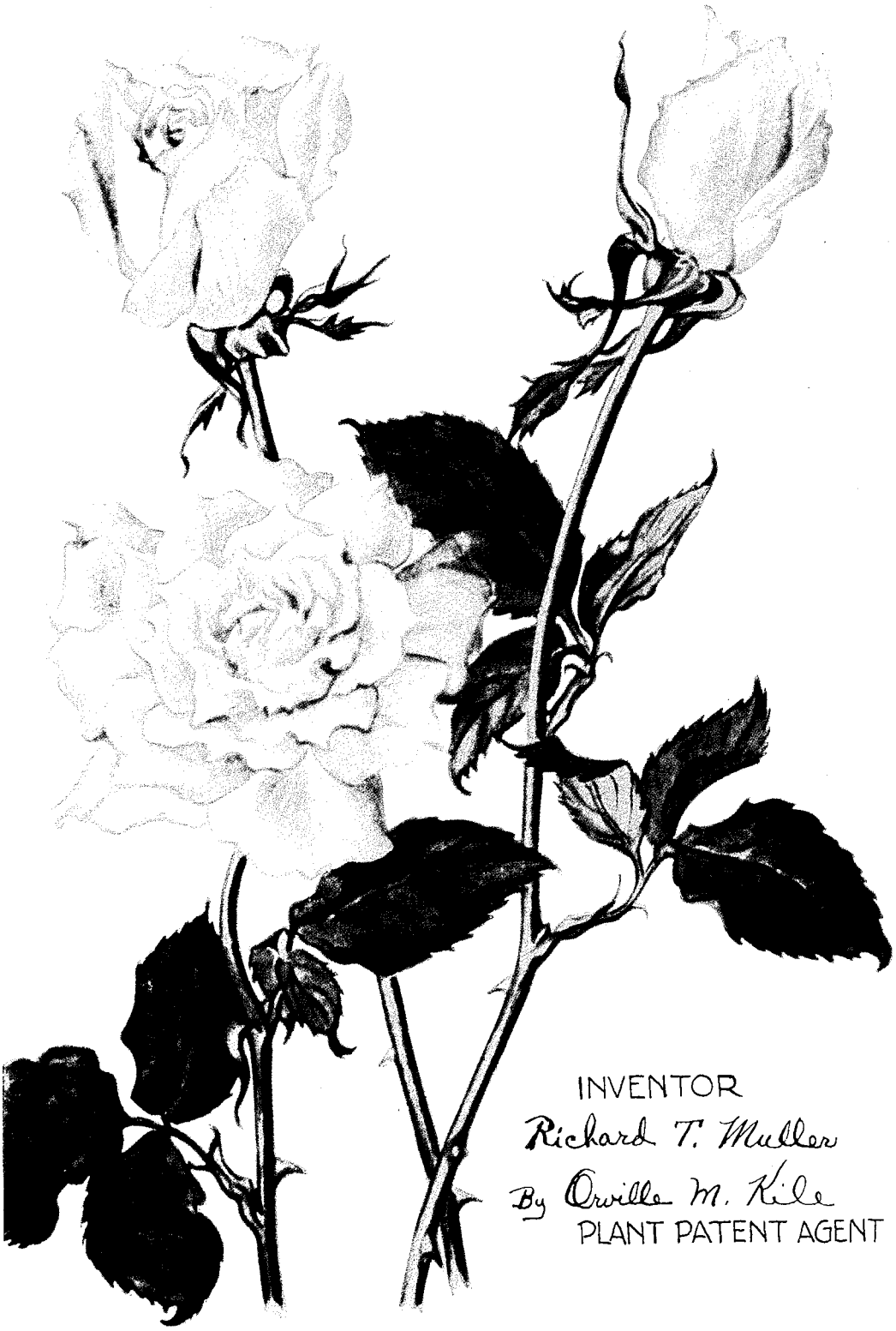

Patented Sept. 29, 1936

Plant Pat. 199

UNITED STATES PATENT OFFICE

199

ROSE

Richard Theodore Muller, Darien, Conn., assignor to The Montgomery Company, Incorporated, Hadley, Mass.

Application April 10, 1936, Serial No. 73,758

1 Claim. (Cl. 47—61)

My present invention relates to a new and improved variety of hybrid tea rose plant, having a deep pink bloom and involving other desirable qualities.

This new variety is a seedling resulting from a cross of the varieties Premier and Talisman—Premier being the female parent.

One of the dominant features of this variety is its perfection of bud when opening from a tight cut bud. This enables the rose to be cut in the bud form and is consequently in excellent condition for shipping and rehandling.

The following is a detailed description of this new variety and the color references are to Ridgway's Color Standards and Nomenclature.

*The plant*

*Form.*—Upright, moderately bushy, throwing out long growths from both the cut-backs and pinches.

*Growth.*—Vigorous and healthy grower, making plants four feet tall in first season. Very free bloomer.

*Foliage.*—Plentiful, leading leaflet 2¾ to 3 inches long, rather broad for its length. Upper surfaces smooth and semi-glossy; serrations rather small and regular; veins not prominent. Color forest green (Plate XVII).

*Rachis.*—Has two or three hard raised places, apparently rudimentary thorns.

*Peduncle.*—Five to five and one-half inches long, straight, rather heavy, light bice green color (Plate XVII).

*Stipules.*—Medium to broad, ending in sharp non-curling points.

*Sepals.*—Long and foliaceous, some reaching a length of 2¾ inches.

*Stems.*—Medium heavy; rather straight.

*Thorns.*—None on first 7 to 9 inches below flower, then rather numerous, medium large, straight but downward pointing.

*The flower*

Buds:

*Form.*—Pointed rather than urn or cup shaped. Tendency for edge of one or more petals to curl back sharply. Open perfectly.

*Color.*—Dominant color effect of the opening bud is Tyrian Rose (Plate XII).

Bloom:

*Size.*—Medium. 2 to 2½ inches across when in prime condition.

*Form.*—Cupped effect in center.

*Petalage.*—Medium fullness, having 28 to 30 petals in December.

*Shape of petals.*—One of the distinguishing features of this variety is the peculiar sharp pointed protuberance at the top of each of the petals, particularly those of the outer four or five rows which are the longer and more noticeable. The shape of the petal otherwise is rounded. The outer two or three rows are rather large petals, being 2 inches or more in width, but most of the petals are only 1 to 1¼ inches wide and of about the same length.

*Color.*—As the rose fully opens it becomes lighter, between "rose color" and "deep rose pink" (Plate XII). It is a somewhat deeper shade on the inside surfaces of the petals than on the outside. Each petal has a small yellowish area at the point of attachment, visible equally from either side of the petal but is confined and does not suffuse the petal. As the inner rows of petals are reached this area elongates into a white streak running the full length of the petal. This streak even appears on an occasional outer petal. The veining is very slight and the coloring even except that it is a somewhat darker shade at the outer edges.

*Lasting qualities.*—Excellent.

*Fragrance.*—Notably fragrant.

Reproductive Organs:

*Stamens.*—Numerous, pink, of about same length as pistils.

*Anthers.*—Buff-colored, large, flat.

*Pistils.*—Moderately numerous, relatively short filaments, white in color except that waxy white tops are streaked with red.

*Filaments.*—Short.

*Ovaries.*—Surrounded by much pithy material.

*Hips.*—Medium width, somewhat tapering.

*Comparison*

The rose most nearly like our rose is Premier but it differs from our variety in many respects. Both roses are a deep pink color but our variety is a brighter more uniform pink both on the outside and inside of the petals. Our variety has a very much more perfectly formed bud which opens fully from the tightly furled cut bud, whereas one of Premier's worst characteristics is that the bud does not open freely when cut. The free opening from a tight bud makes our variety a more desirable shipping variety.

Having thus disclosed my invention, what I claim is:

The new and distinct variety of Hybrid Tea Rose plant herein described and shown, characterized particularly by its perfection of form of bud and flower, the purity and vividness of its pink color as shown, its quality of freely opening from tightly furled cut buds, and its vigorous and healthy growth.

RICHARD T. MULLER.